United States Patent
Threlkeld et al.

(10) Patent No.: US 11,076,885 B2
(45) Date of Patent: Aug. 3, 2021

(54) CATHETER REMOVAL INSTRUMENTS AND METHODS

(71) Applicant: OCEAN MEDICAL LLC, Fife, WA (US)

(72) Inventors: Judson E. Threlkeld, Camas, WA (US); Joseph A. Hare, Spokane, WA (US)

(73) Assignee: OCEAN MEDICAL, LLC, Fife, WA (US)

( * ) Notice: Subject to any disclaimer, the term of this patent is extended or adjusted under 35 U.S.C. 154(b) by 158 days.

(21) Appl. No.: 16/174,065

(22) Filed: Oct. 29, 2018

(65) Prior Publication Data
US 2019/0125402 A1    May 2, 2019

Related U.S. Application Data

(60) Provisional application No. 62/579,060, filed on Oct. 30, 2017.

(51) Int. Cl.
*A61B 17/34* (2006.01)
*A61B 17/29* (2006.01)
(Continued)

(52) U.S. Cl.
CPC ........ *A61B 17/3468* (2013.01); *A61B 17/282* (2013.01); *A61B 17/29* (2013.01);
(Continued)

(58) Field of Classification Search
CPC ....... A61B 17/28; A61B 17/282; A61B 17/29; A61B 2017/2926; A61B 17/3468; A61M 2025/024
See application file for complete search history.

(56) References Cited

U.S. PATENT DOCUMENTS 2,644,455 A    7/1953  Benoit
5,133,724 A *  7/1992  Wilson, Jr. ........... A61B 17/122
                                                  606/151
(Continued)

FOREIGN PATENT DOCUMENTS

WO    WO 2017/029504    2/2017
WO    PCT/US18/58016    1/2019

*Primary Examiner* — Wade Miles
(74) *Attorney, Agent, or Firm* — R. Reams Goodloe, Jr.

(57) ABSTRACT

Catheter removal instruments are provided that can include: at least a pair of instrument jaws aligned along the same axis and opposing one another when engaged, each of the jaws defining recesses having openings wherein the openings of each jaw oppose one another; and a plurality of tips and valleys within the recess with the tips extending toward the openings of each of the jaws, and each of the tips of one jaw aligned opposing the tip of another jaw when the jaws are engaged. Catheter removal instruments are also provided that can include: at least a pair of instrument jaws aligned along the same axis and opposing one another when engaged, each of the jaws defining recesses having openings wherein the openings of each jaw oppose one another; and wherein each of the jaws defines a semi-round channel having a smooth outer surface.
Methods for removing a catheter are provided that can include working a pair of opposing semi-round channeled jaws over a brace to free the brace of dermis engaged with the brace; and removing the catheter. Methods for removing a catheter are also provided that can include engaging a catheter tube below the dermis with a plurality of tips extending from individual opposing jaws to remove the catheter.

26 Claims, 5 Drawing Sheets

(51) Int. Cl.
*A61B 17/28* (2006.01)
*A61B 17/3205* (2006.01)
*A61B 17/00* (2006.01)
*A61B 17/32* (2006.01)
*A61M 25/01* (2006.01)

(52) U.S. Cl.
CPC .. *A61B 17/32053* (2013.01); *A61B 17/00008* (2013.01); *A61B 2017/2945* (2013.01); *A61B 2017/320056* (2013.01); *A61M 25/01* (2013.01)

(56) References Cited

U.S. PATENT DOCUMENTS

| | | | | |
|---|---|---|---|---|
| 5,222,973 A | * | 6/1993 | Sharpe | A61B 17/29 294/100 |
| 5,241,090 A | | 8/1993 | Orzi et al. | |
| 5,354,312 A | * | 10/1994 | Brinkerhoff | A61B 17/29 606/205 |
| 5,398,679 A | * | 3/1995 | Freed | A61M 16/0488 128/207.17 |
| 5,482,054 A | * | 1/1996 | Slater | A61B 1/0064 600/564 |
| 5,555,881 A | * | 9/1996 | Rogers | A61M 16/0488 128/207.14 |
| 5,693,069 A | | 12/1997 | Shallman | |
| 6,361,541 B1 | | 3/2002 | Barnhart | |
| 7,258,685 B2 | | 8/2007 | Kerr | |
| 7,758,590 B2 | | 7/2010 | Daniele et al. | |
| 8,372,098 B2 | | 2/2013 | Tran | |
| 9,186,204 B2 | * | 11/2015 | Nishimura | A61B 18/1445 |
| 10,052,128 B2 | * | 8/2018 | Herscu | A61M 25/0017 |
| 2005/0004590 A1 | * | 1/2005 | Waters | A61B 17/282 606/170 |
| 2006/0184198 A1 | * | 8/2006 | Bales | A61B 10/06 606/205 |
| 2007/0185510 A1 | | 8/2007 | Tran | |
| 2007/0244490 A1 | | 10/2007 | Moehle | |
| 2007/0244511 A1 | * | 10/2007 | Weizman | A61B 10/06 606/205 |
| 2008/0177297 A1 | * | 7/2008 | Steiner | A61B 17/282 606/205 |
| 2009/0177196 A1 | * | 7/2009 | Zlock | A61B 17/7083 606/53 |
| 2009/0264897 A1 | * | 10/2009 | Wohl | A61B 17/24 606/110 |
| 2010/0262176 A1 | | 10/2010 | Peartree | |
| 2010/0274278 A1 | * | 10/2010 | Fleenor | A61B 17/29 606/206 |
| 2010/0292724 A1 | * | 11/2010 | Ravikumar | A61B 17/221 606/185 |
| 2012/0203240 A1 | | 8/2012 | Delahoussaye et al. | |
| 2016/0331408 A1 | * | 11/2016 | Benson | A61B 17/4241 |
| 2017/0007344 A1 | * | 1/2017 | Seow | A61B 34/30 |
| 2017/0056045 A1 | | 3/2017 | Herscu et al. | |
| 2017/0071585 A1 | * | 3/2017 | Adkisson | A61B 10/06 |
| 2017/0238956 A1 | * | 8/2017 | Dam-Huisman | A61F 9/00709 |
| 2018/0303507 A1 | * | 10/2018 | Suzuki | A61B 17/29 |
| 2020/0060685 A1 | * | 2/2020 | Han | A61B 17/122 |

* cited by examiner

CATHETER REMOVAL INSTRUMENTS AND METHODS

CROSS REFERENCE TO RELATED APPLICATION

This application claims priority to and the benefit of U.S. Provisional Patent Application Ser. No. 62/579,060 filed Oct. 30, 2017, entitled "Catheter Removal Instruments and Methods", the entirety of which is incorporated by reference herein.

TECHNICAL FIELD

The present disclosure relates generally to medical devices and more specifically to catheter removal instruments and methods.

BACKGROUND

Catheters can be placed within patients for extended periods of time. These catheters include portions that are meant to mend or bind with the dermis of the patient, so that the catheter can be manipulated externally with little impact to the internal connection of the catheter. Gratefully, these catheters can be removed, and when removed, it is important to be able to inflict as little damage to the dermis of the patient, or the patient, as practical. The present disclosure provides catheter removal instruments and methods.

SUMMARY

Catheter removal instruments are provided that can include: at least a pair of instrument jaws aligned along the same axis and opposing one another when engaged, each of the jaws defining recesses having openings wherein the openings of each jaw oppose one another; and a plurality of tips and valleys within the recess with the tips extending toward the openings of each of the jaws, and each of the tips of one jaw aligned opposing the tip of another jaw when the jaws are engaged.

Catheter removal instruments are also provided that can include: at least a pair of instrument jaws aligned along the same axis and opposing one another when engaged, each of the jaws defining recesses having openings wherein the openings of each jaw oppose one another; and wherein each of the jaws define a semi-round channel having a smooth outer surface.

Methods for removing a catheter are provided that can include working a pair of opposing semi-round channeled jaws over a brace to free the brace of dermis engaged with the brace, and removing the catheter Methods for removing a catheter are also provided that can include engaging a catheter tube below the dermis with a plurality of tips extending from individual opposing jaws to remove the catheter.

DRAWINGS

Embodiments of the disclosure are described below with reference to the following accompanying drawings.

DESCRIPTION

This disclosure is submitted in furtherance of the constitutional purposes of the U.S. Patent Laws "to promote the progress of science and useful arts" (Article 1, Section 8).

Figure 1:
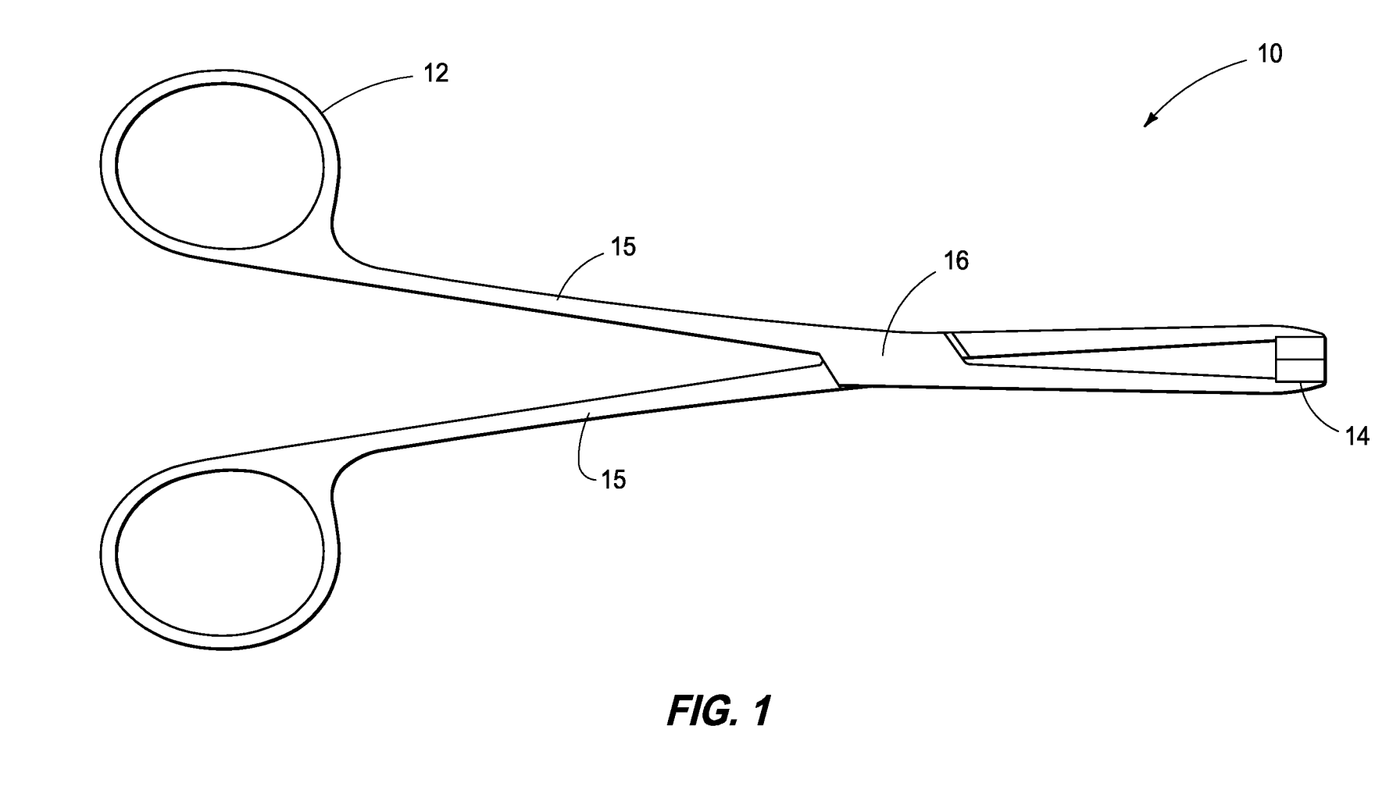
FIG. 1 is a catheter removal assembly according to an embodiment of the disclosure.

The present disclosure will be described with reference to FIGS. 1-10. Referring first to FIG. 1, a catheter removal assembly 10 is shown that includes a digitally manipulative portion 12 extended to at least a pair of jaws 14 supported by arms 15 that may be hinged at a central location 16 between the manipulative portion and the jaws. Jaws 14 can be aligned along the same axis and opposing one another when engaged as shown. In accordance with example implementations, assembly 10 can be manipulated wherein when the user exerts gripping pressure upon end 12, the jaws 14 constrict, tightens, or close. Alternatively, when the user exerts expanding digital pressure, jaws 14 retract, expand, or open.

Figure 2:
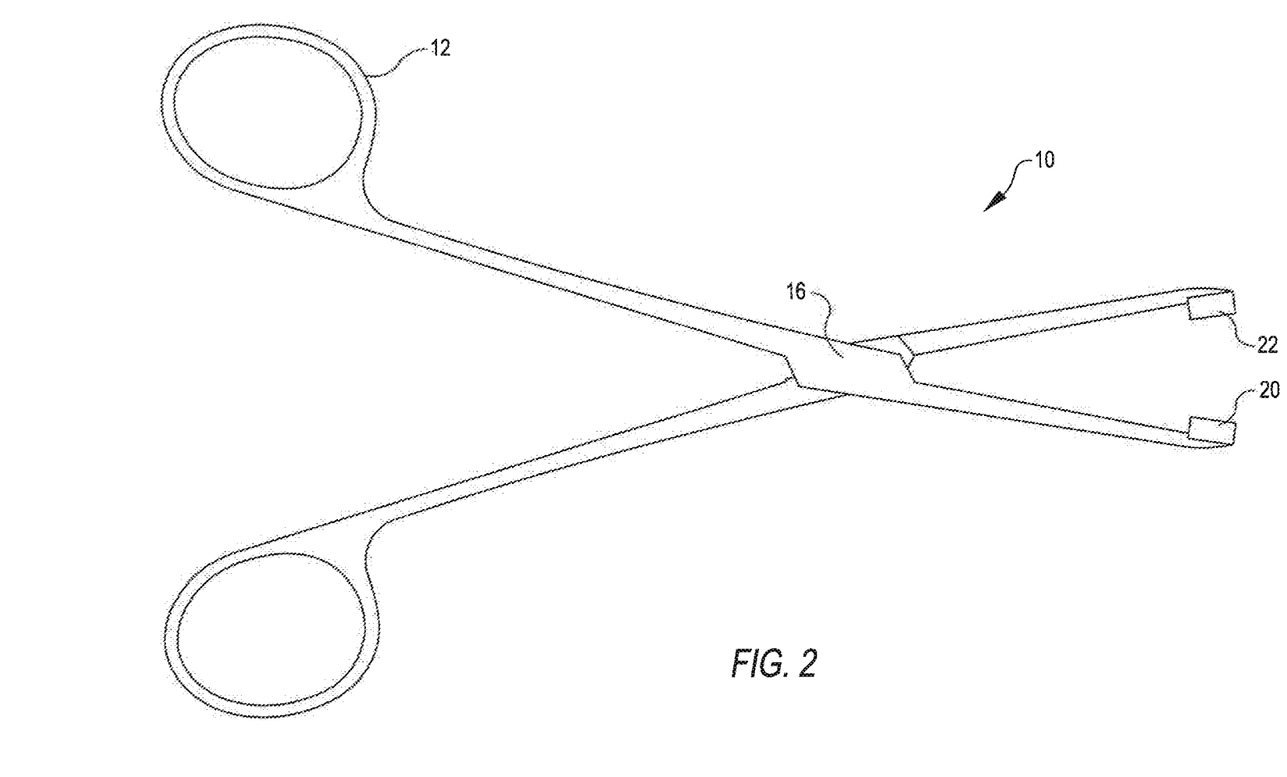
FIG. 2 is the assembly of FIG. 1 in an alternate configuration.

Referring next to FIG. 2, assembly 10 is shown in an alternative configuration with jaws 14 retracted or expanded. As can be seen, jaws 14 can include two opposing jaws 20 and 22. Either or both of jaws 14 can be configured to manipulate the dermis about a catheter and free the catheter from the dermis as well as, for example, grip the catheter for extraction.

Figure 3:
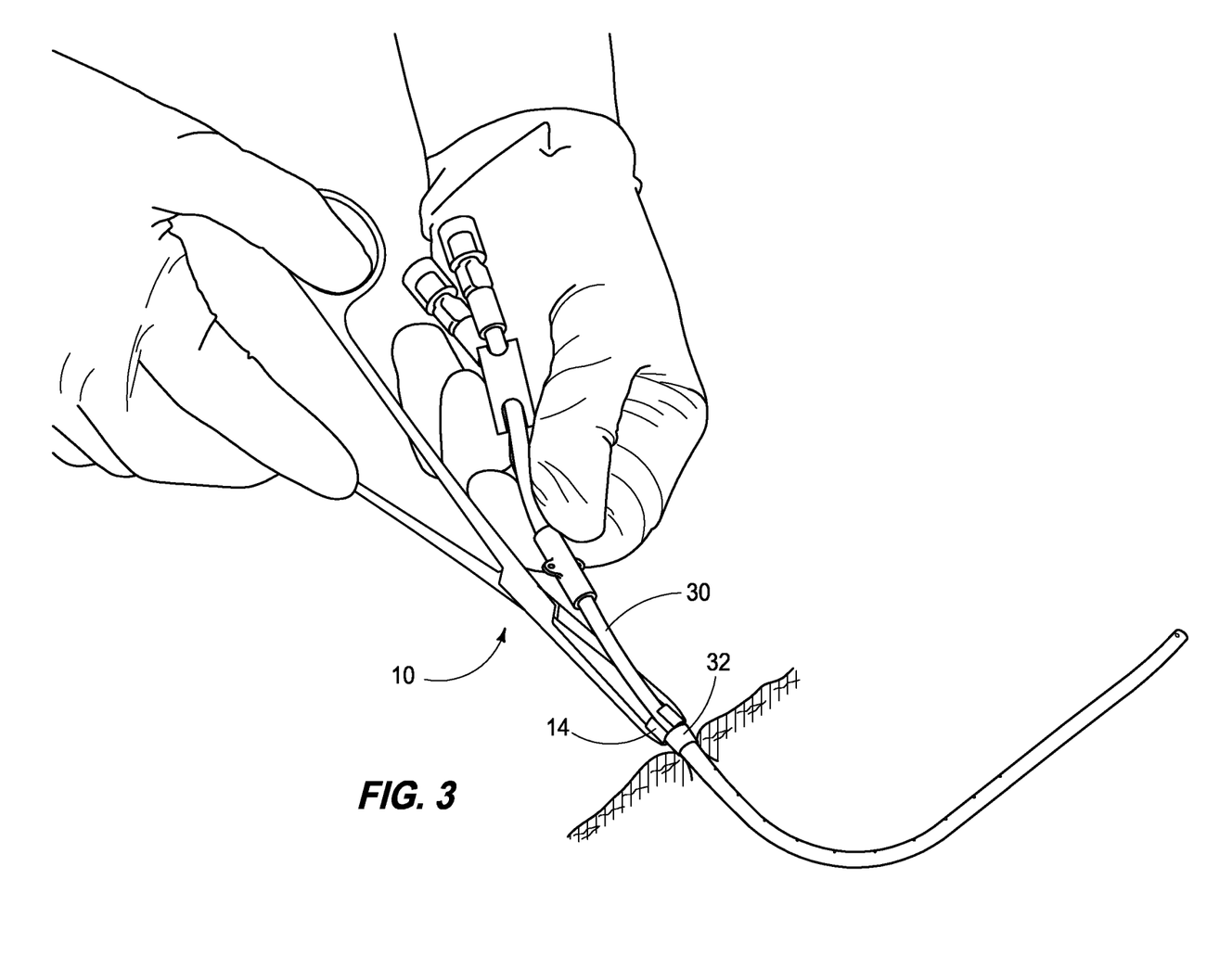
FIG. 3 depicts the use of the assemblies of FIGS. 1 and 2 at an initial phase of catheter removal.
Figure 4:
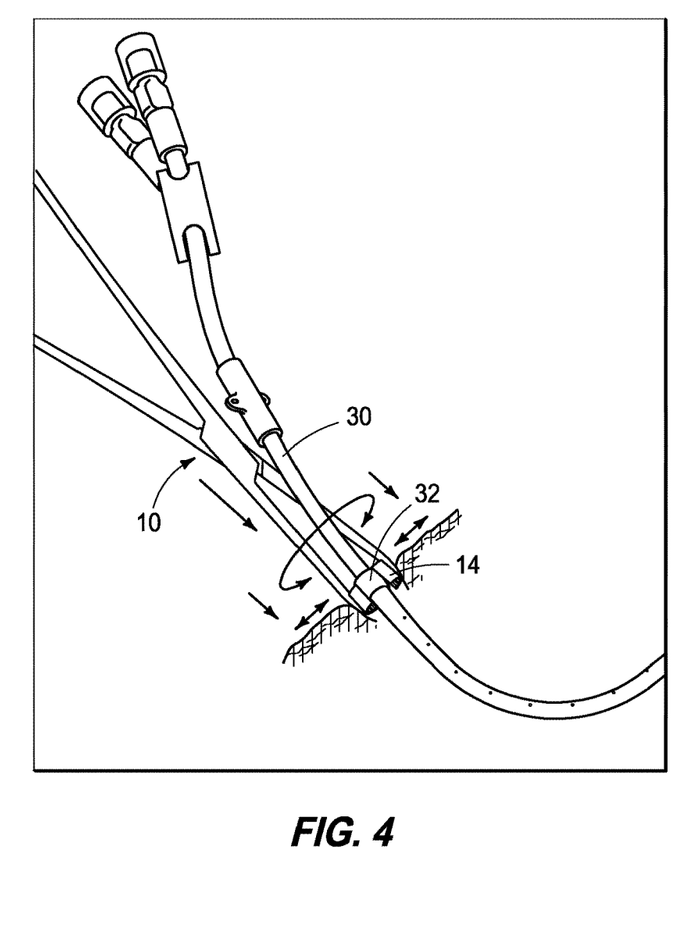
FIG. 4 depicts the use of the assemblies of FIGS. 1 and 2 at a subsequent phase of catheter removal to that of FIG. 3.
Figure 5:
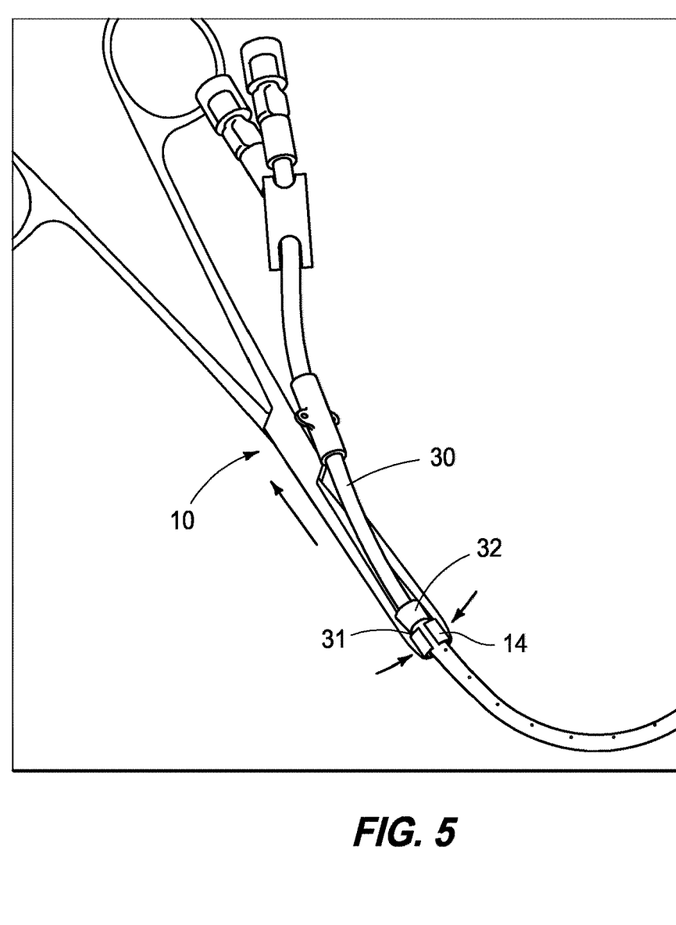
FIG. 5 depicts the use of the assemblies of FIGS. 1 and 2 at a subsequent phase of catheter removal to that of FIG. 4.

Referring next to FIGS. 3-5, assembly 10 can be used to manipulate a catheter 30. Catheter 30 can have a sponge or brace 32 extending along a distance of the catheter. This sponge or brace 32 can be sufficiently fibrous to mend or join with the dermis of the patient when in use. Typically, this sponge or brace may have an outer perimeter that is larger than the outer perimeter of the catheter tubing. As shown in FIG. 3, assembly 10 can be used to manipulate over the catheter itself and about the sponge or brace 32. In accordance with example implementations, jaws 14 can be worked over brace 32 to free brace 32 of the dermis to which it is bound.

Referring next to FIG. 4, as can be seen, the curved nature of jaws 14 in combination with extending force from the user as well as expanding pressure from the digits of the user can be used to allow jaws 14 to extend about brace 32. Accordingly, jaws 14 can be worked away from one another against the dermis as shown. Jaws 14 can be extended along the sides of brace 32. Jaws 14 can also be rotated about the axis of the catheter tube.

With reference to FIG. 5, jaws 14 can be worked past brace 32. Once past brace 32, clamping pressure can be exerted by the operator, allowing jaws 14 to collapse about catheter 30 on the internal side of brace 32, and then pulling force can be applied to remove catheter 30 from the patient. In some applications, jaws 14 can be clamped about the brace or to grab the brace and force exerted to remove the catheter while clamping the brace. In accordance with at least one implementation, tips extending from jaws 14 can engage the catheter tube. Other or additional implementations in combinations or separately can include engaging brace 32 with a proximal edge 31 of jaws 14. Additionally, engaged jaws 14 may be rotated about the axis of the catheter tube to remove the catheter.

Figure 6:
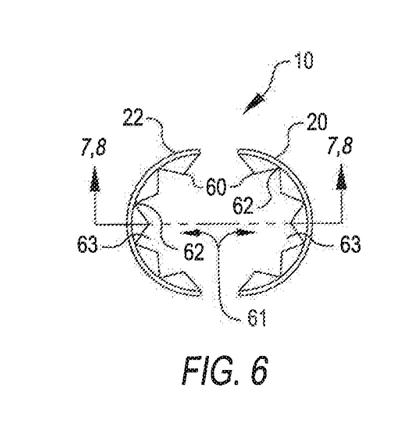
FIG. 6 is a detailed view of a portion of the assemblies of FIGS. 1 and 2 according to an embodiment of the disclosure.

Referring next to FIG. 6, an end view of jaw 14 is shown. As can be seen in this view, jaws 14 can include opposing jaws that can be at least partially cylindrical. In accordance with example implementations, each jaw may define a recess 63 having openings 61. These openings 61 can oppose one another. A plurality of tips 60 and valleys 62 can be within recess 63 with tips 60 extending from recess 63. Each tip 60 and/or valley 62 can be aligned opposing one another when jaws 14 are in the closed position for example.

Figure 7:
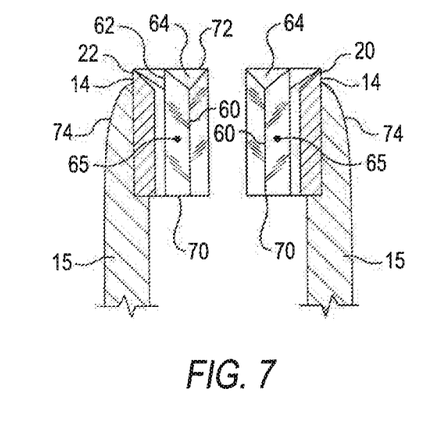
FIG. 7 is a detailed cross-sectional view of a portion of the assemblies of FIGS. 1 and 2 according to an embodiment of the disclosure.

Referring next to FIG. 7, in accordance with one embodiment, jaws 14 may be configured where the shape defined by tips 60 and valleys 62 in which the exposed portions substantially form triangular prisms 65 where valleys 62 provide veins that extend the distance of the jaws, from one end entirely to the other end, for example, from terminus 70 at a proximal end entirely to terminus 72 at a distal end. As can be seen, the triangular prisms 65 can include a beveled portion 64. Additionally, arms 15 can be tapered or rounded at, for example end 74 to facilitate the engagement of jaws 14 with the dermis.

Figure 8:
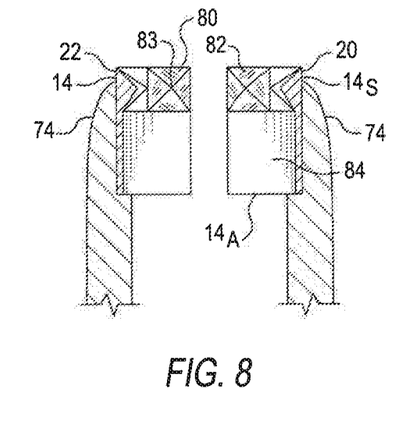
FIG. 8 depicts another implementation of a portion of FIG. 7 according to an embodiment of the disclosure.

Referring next to FIG. 8, in accordance with an alternative embodiment, jaws 14 can include a toothed configuration rather than a veined configuration. The toothed configuration can include individual teeth 80 that may include one or more beveled portions 82. Example implementations may include four beveled portions 64 to give each tooth 80 a central point 83 with bevels about each of the points. In accordance with alternative embodiments, tooth 80 may include a flat edge towards the proximate portion and the front bevel towards the distal portion of the tooth 80. Accordingly, teeth 80 can extend from a portion of jaws 14. For example, teeth 80 can extend from a distal portion of jaw 14. In example implementations, the remaining interior surface 84 of jaws 14 can be smooth. As can be seen by comparing FIGS. 6 and 8, the jaws 14 may be provided by a pair of thin half-cylindrical annulus shapes with an outer surface 14$_s$ and inner surface 84, and wherein triangular prisms 65 are mounted (FIG. 7), or teeth 80 are mounted (FIG. 8).

Figure 9:
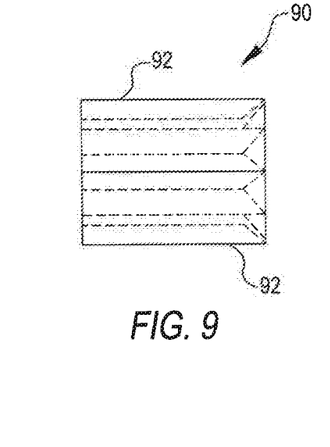
FIG. 9 is a side view of a portion of the assemblies of FIGS. 1 and 2 according to an embodiment of the disclosure.
Figure 10:
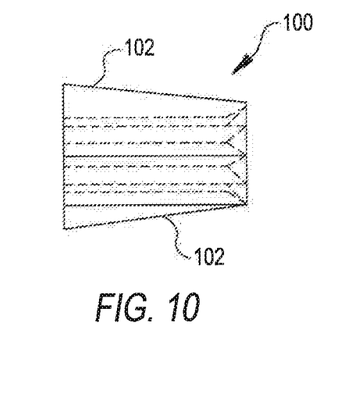
FIG. 10 is a side view of a portion of the assemblies of FIGS. 1 and 2 according to an embodiment of the disclosure.

Referring next to FIGS. 9 and 10, alternative embodiments of the jaws are shown with jaws 90, for example, having a relatively straight edge extending from the distal portion to the rearward portion of the tip. In accordance with example implementations, jaws 14 are defined by a semi-round channel having a smooth outer surface 92.

With regard to FIG. 10, jaws 100 can include a frustal conical configuration wherein the distal portion of the jaws has a smaller radius than the rearward portion, giving rise to a slight angular difference between the front edge member and the rear edge member of tip jaws 100. Additionally, in this configuration, jaws 14 are defined to have a smooth outer surface 102.

The present assembly can be manufactured of medical grade steel suitable for sterilization as desirable.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect.

The invention claimed is:

1. A catheter removal instrument for removal of a catheter at an interface of the catheter with a portion of dermis of a patient, comprising:

two instrument arms each extending along an instrument arm axis, the two instrument arms pivoted together at a hinge, each instrument arm comprising a digitally manipulative portion at a proximal end and a jaw portion at a distal end, each jaw portion having a jaw, with each jaw oriented to face toward the jaw portion on which an opposing jaw is mounted, and wherein each jaw has an opening directed inwardly toward the other jaw and inwardly toward the instrument arm on which the opposing jaw is mounted, and wherein the distal end of each jaw portion is tapered toward the distal end of the jaw located on each jaw portion, so as to facilitate engagement of the jaw portions with a portion of the dermis of a patient, and wherein the jaws are each configured as at least partially curve shaped jaws which are located along their respective instrument arm to oppose each other when brought together, so that in use, the two opposing at least partially curve shaped jaws together clasp substantially around a catheter to be removed;

wherein the jaws each include recesses having openings, wherein the openings oppose one another when the jaws are moved toward each other, and wherein the openings are defined by tips and valleys in the opening of each jaw, and wherein the tips and valleys extend along and within the jaws in a direction substantially along the axis of the instrument arm on which the jaw is mounted.

2. The catheter removal instrument as set forth in claim 1, wherein each of the tips and valleys extend along the axis of the instrument arm on which the jaw is mounted for a distance, wherein the tips and valleys provide a toothed configuration.

3. The catheter removal instrument as set forth in claim 1, wherein each jaw comprises a tooth portion at or near the distal end, and a smooth portion extending inwardly from the tooth portion to a terminus at a proximal end, along the axis of the instrument arm on which the jaw is located.

4. The catheter removal instrument as set forth in claim 3, wherein each tooth portion comprises a plurality of teeth.

5. The catheter removal instrument as set forth in claim 4, wherein the plurality of teeth each further comprise one or more beveled portions.

6. The catheter removal instrument as set forth in claim 5, wherein the one or more beveled portions comprise a distal beveled portion.

7. The catheter removal instrument as set forth in claim 6, wherein each of the plurality of teeth has a distal side and a proximate side, and wherein each of the plurality of teeth further comprises a flat edge at the proximate side.

8. The catheter removal instrument as set forth in claim 5, wherein the plurality of teeth each comprise four beveled portions.

9. The catheter removal instrument as set forth in claim 1, wherein each of the tips and valleys extend along the axis of the instrument arm on which the jaw is mounted for a distance wherein the tips and valleys provide an inside surface which is shaped as a plurality of triangular prisms within the jaw portion, wherein the valleys are formed between adjacent triangular prisms, and the tips are formed at vertices of the triangular prisms.

10. The catheter removal instrument as set forth in claim 9, wherein the triangular prisms in each jaw have distal end coterminous with a distal end of the jaw, and extend inwardly from the distal end to a proximal end coterminous with a proximal end of the jaw, along the axis of the instrument arm on which the jaw is located.

11. The catheter removal instrument as set forth in claim 9, wherein each triangular prism further comprises one or more beveled portions.

12. The catheter removal instrument as set forth in claim 11, wherein the one or more beveled portions comprise a front beveled portion.

13. The catheter removal instrument as set forth in claim 1, wherein each jaw comprises a thin half-cylindrical annulus shape having an inside surface, with a plurality of teeth mounted on the inside surface.

14. The catheter removal instrument as set forth in claim 1, wherein each jaw comprises a thin half-cylindrical annulus shape having an inside surface, wherein the inside surface is shaped as a plurality of triangular prisms mounted on the inside surface.

15. The catheter removal instrument as set forth in claim 1, wherein each jaw comprises a thin one-half frusto-conical shape having an inside surface, where the frusto-conical shape has a distal end and a proximal end, and wherein the proximal end is larger in diameter than the distal end, and wherein a plurality of teeth are mounted on the inside surface.

16. The catheter removal instrument as set forth in claim 1, wherein each jaw comprises a thin half-cylindrical annulus shape having an outside surface, and wherein the outside surface is smooth.

17. The catheter removal instrument as set forth in claim 1, wherein the distal end of each jaw portion is tapered.

18. The catheter removal instrument as set forth in claim 1, wherein the distal end of each jaw portion is rounded.

19. A method for removing a catheter at an interface of the catheter with a dermis portion of a patient with the catheter removal instrument set forth in claim 1, comprising:
providing the two instrument arms;
working the jaws over a brace to free the brace of dermis engaged with the brace;
expanding digital pressure against the instrument arms supporting the jaws to move the jaws away from one another and against the dermis during the working; and
removing the catheter.

20. The method of claim 19 wherein the brace has side portions, and wherein the working comprises extending the jaws along the side portions of the brace.

21. The method of claim 19 wherein the catheter comprises a tube extending along an axis, and wherein the working comprises rotating the jaws about the axis of the tube.

22. A method for removing a catheter at an interface of the catheter with a dermis portion of a patient with the catheter removal instrument set forth in claim 1, comprising:
providing the catheter removal instrument;
engaging a catheter tube below the dermis with the tips; and
removing the catheter, by providing outward force on the catheter via the catheter removal instrument.

23. The method of claim 22 further comprising extending the jaws over a brace before engaging the catheter.

24. The method of claim 23 further comprising engaging a distal portion of the brace with the tips to remove the catheter.

25. The method of claim 22 further comprising digitally manipulating the instrument arms supporting the jaws to remove the catheter.

26. The method of claim 25 wherein the digitally manipulating comprises rotating the engaged jaws about the axis of the catheter tube to remove the catheter.

* * * * *

UNITED STATES PATENT AND TRADEMARK OFFICE
CERTIFICATE OF CORRECTION

Page 1 of 1

PATENT NO. : 11,076,885 B2
APPLICATION NO. : 16/174065
DATED : August 3, 2021
INVENTOR(S) : Judson E. Threlkeld and Joseph A. Hare It is certified that error appears in the above-identified patent and that said Letters Patent is hereby corrected as shown below:

On the Title Page

On the second page, item (56) under "References Cited, U.S. Patent Documents" delete:
"5241090 A 8/1993 Orzi, et al"

And substitute therefore:
--5421090 A 1995-06-06 Chiou--

In the Specification

Column 3, Line 40, after the words "from a distal portion of", delete:
"jaw"

And substitute therefore:
--jaws--.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*